(12) United States Patent
Yousefi et al.

(10) Patent No.: US 10,945,598 B2
(45) Date of Patent: Mar. 16, 2021

(54) METHOD FOR ASSISTING CORNEAL SEVERITY IDENTIFICATION USING UNSUPERVISED MACHINE LEARNING

(71) Applicants: JICHI MEDICAL UNIVERSITY, Tokyo (JP); Takahiko Hayashi, Yokohama (JP)

(72) Inventors: Siamak Yousefi, Memphis, TN (US); Hidenori Takahashi, Shimotsuke (JP); Takahiko Hayashi, Yokohama (JP)

(73) Assignee: JICHI MEDICAL UNIVERSITY

( * ) Notice: Subject to any disclaimer, the term of this patent is extended or adjusted under 35 U.S.C. 154(b) by 89 days.

(21) Appl. No.: 16/269,221

(22) Filed: Feb. 6, 2019

(65) Prior Publication Data

US 2020/0245865 A1 Aug. 6, 2020

(51) Int. Cl.
| | |
|---|---|
| *G06K 9/00* | (2006.01) |
| *A61B 3/107* | (2006.01) |
| *A61B 3/10* | (2006.01) |
| *G16H 50/70* | (2018.01) |
| *A61B 3/00* | (2006.01) |

(52) U.S. Cl.
CPC .............. *A61B 3/107* (2013.01); *A61B 3/102* (2013.01); *A61B 3/1005* (2013.01); *A61B 3/0041* (2013.01); *G16H 50/70* (2018.01)

(58) Field of Classification Search
CPC ... G06T 7/0012; G06T 7/0081; G06T 7/0083; G06T 11/003; G06T 2207/10081; G06T 2207/30004; A61B 6/0306; A61B 3/107; G06F 19/321
See application file for complete search history.

(56) References Cited

U.S. PATENT DOCUMENTS

| | | | | |
|---|---|---|---|---|
| 5,589,451 A | * | 12/1996 | Wilson ............... | A61K 38/1833 435/377 |
| 5,767,079 A | * | 6/1998 | Glaser ................ | A61K 38/1841 424/427 |
| 6,124,259 A | * | 9/2000 | Delmage ............ | A61K 38/1709 435/69.1 |

(Continued)

FOREIGN PATENT DOCUMENTS

| | | |
|---|---|---|
| JP | 2005-288176 | 5/2008 |
| JP | 2010-057897 | 3/2010 |
| JP | 2013-255791 | 12/2013 |

OTHER PUBLICATIONS

Souza, Murilo Barreto, et al. *Evaluation of machine learning classifiers in keratoconus detection from orbscan II examinations*, Clinics 2010; 65(12) pp. 1223-1228, 2010.

(Continued)

*Primary Examiner* — Amir Alavi
(74) *Attorney, Agent, or Firm* — Fay Sharpe LLP

(57) ABSTRACT

A method for assisting corneal severity identification, the method comprising obtaining a corneal configuration data set of a cornea to be examined by a tomography such as an optical coherence tomography; visualizing the corneal configuration data set of the cornea to be examined along with a number of pre-existing corneal configuration data sets of disorder corneas, disorder-suspect corneas and normal corneas obtained by the tomography using t-distributed Stochastic Neighbor Embedding in a two or three dimensional map, and judging corneal severity from the map.

14 Claims, 13 Drawing Sheets

(56) References Cited

U.S. PATENT DOCUMENTS

| | | | | |
|---|---|---|---|---|
| 6,927,888 | B2* | 8/2005 | Garcia | G02B 5/3025 |
| | | | | 356/369 |
| 7,281,801 | B2* | 10/2007 | Wang | A61B 3/101 |
| | | | | 351/205 |
| 8,746,883 | B2* | 6/2014 | Korb | A61B 3/14 |
| | | | | 351/206 |
| 8,888,286 | B2* | 11/2014 | Grenon | A61B 3/1005 |
| | | | | 351/206 |
| 8,915,592 | B2* | 12/2014 | Korb | A61B 3/0025 |
| | | | | 351/206 |
| 9,522,160 | B2* | 12/2016 | McVicar | A61K 31/14 |
| 9,744,076 | B2* | 8/2017 | da Silva Curiel | A61F 9/00781 |
| 9,795,290 | B2* | 10/2017 | Grenon | G01B 11/06 |
| 2005/0225724 | A1 | 10/2005 | Klyce et al. | |
| 2010/0060854 | A1 | 3/2010 | Bille | |
| 2013/0329187 | A1 | 12/2013 | Steinmueller | |
| 2018/0030515 | A1* | 2/2018 | Regev | C12Q 1/6809 |

OTHER PUBLICATIONS

Hidalgo, Irene Ruiz et al. *Evaluation of a Machine-Learning Classifier for Keratoconus Detection Based on Scheimpflug Tomography*, Cornea vol. 35, No. 6, Jun. 2016, pp. 827-832.

*Program Schedule*, 2018 ARVO Imaging in the Eye Conference Apr. 28, 2018, Apr. 2018, 14 pages.

McMahon, TT. et al., *A new method for grading the severity of keratoconus: the Keratoconus Severity Score (KSS)* Cornea, Aug. 2006; 25(7); (Abstract only).

Yousefi, Siamak et al. *Keratoconus severity identification using unsupervised learning and density-based clustering applied to big corneal data*, The University of Tennessee Health Science Center, Data Mining and Machine Learning Lab, published Apr. 28, 2018.

Yousefi, Siamak et al. *Keratoconus severity identification using unsupervised machine learning*, PLOS One, 13(11): e0205998, pp. 1-11, Nov. 6, 2018.

Van der Maaten, Laurens et al., *Visualizing Data using t-SNE*, Journal of Machine Learning Research 9 (2008) pp. 2579-2605, Nov. 2008.

Yousefi, Siamak et al. Abstract Submission, Control ID 2965461, *Keratoconus severity identification using unsupervised learning and density-based clustering applied on big corneal data*, 4 pages, accepted Apr. 2018.

Yousefi, Siamak et al. *Keratoconus severity identification using unsupervised machine learning*, PLOS One, 13(11): e0205998, pp. 1-7, Nov. 6, 2018 (printed Nov. 27, 2018).

* cited by examiner

METHOD FOR ASSISTING CORNEAL SEVERITY IDENTIFICATION USING UNSUPERVISED MACHINE LEARNING

TECHNICAL FIELD

The invention is related to a method for assisting corneal severity identification using unsupervised machine learning.

BACKGROUND ART

In corneal diseases, keratoconus, bullous keratopathy, walleye, keratoleukoma, keratohelcosis, herpes corneae, corneal chemical burn, corneal thermal burn, degeneratio corneae and the like can be restored by a corneal transplant. It is difficult to determine need for the transplantation.

Keratoconus is a noninflamatory ectatic corneal disorder characterized by progressive thinning resulting in corneal protrusion and decreased vision (Non-Patent Document 1). Moderate to advanced keratoconus cases are easily diagnosed due to the presence of classic retinoscopic and biomicroscopic signs. However, detecting subclinical keratoconus is challenging because initial manifestations of keratoconus may be unclear, requiring a more comprehensive analysis of corneal characteristics including topography, elevation, thickness, and biomechanical properties (Non-Patent Documents 2 and 3). Many methods have been suggested for identifying keratoconic eyes using corneal topography information. However, most of the methods rely on subjective analysis of topographical maps which can be biased by the observer (Non-Patent Document 4).

Among objective approaches for keratoconus identification, machine learning analysis has gained a lot of attension. Smolek and Klyce (Non-Patent Document 5) proposed a neural network for keratoconus screening based on corneal topography indices. Chastang et al. (Non-Patent Document 6) introduced a binary decision trees method based on corneal topography indices to identify clinically apparent keratoconus from normal cornea. A similar approach was used a few years later to identify keratoconus from normal corneas using corneal surface modeled with a seventh-order Zernike polynomial (Non-Patent Document 7). All these methods used only anterior topography characteristics of cornea. However, with the advancement of technology, posterior corneal curvature and pachymetric data were acquired and used to evaluate corneal characteristics (Non-Patent Document 8). Pinero et al. documented the corneal volume, pachymetry, and correlation of anterior and posterior corneal shape in subclinical and clinical keratoconus (Non-Patent Document 9). Perez et al. show that corneal instruments including videokeratography, Orbscan, and Pentacam together with the indices can lead to early keratoconus detection, however, with an increase in false positive detection (Non-Patent Document 10).

current methods for automatic detection of keratoconus are mainly supervised, in the sense that labels and diagnoses are required as input for subsequent machine learning. We propose an approach that is non-biased by either clinician or patient. This approach may lead to better identification of form fruste keratoconus which can be hard to do clinically in some cases. Moreover, it provides a non-biased method to determine progression and need for other treatment, such as cross-linking (Non-Patent Document 11). From big data perspective, the proposed approach is objective without the need to pre-label the eyes. Our results suggest that unsupervised machine learning can be applied to corneal topography, elevation, and pachymetry parameters to generate highly specific and sensitive models.

Additionally, Patent Document 1 discloses a method for diagnosing a keratoconus cornea in an eye of a patient which comprises the steps of: providing an electronic model of a cornea, wherein the model includes a plurality of elements, and wherein each element in the model is defined by a plurality of parameters, with each parameter being representative of tissue qualities in the cornea at the corresponding location of the element in the model; mapping a topography of the anterior surface of the cornea "Ta"; fitting the topography "Ta" to the model to obtain a set of parameters for the plurality of elements; and evaluating the set of parameters to diagnose whether the cornea is keratoconus.

Patent Document 2 discloses a method for measuring a cornea of an eye said method comprising: measuring a topography of a cornea experiencing a change in intraocular pressure using an ophthalmological analysis system during a measurement time interval; obtaining a number of image data sets of a surface area of the cornea during the measurement time interval, wherein, in the measurement time interval, due to said change in the intraocular pressure, a repeated change in the topography of the cornea in the measurement time interval is caused; and determining the repeated change in the topography of the cornea from the number of image data sets, wherein, in each case, the change is measured for points (P) of the surface area of the cornea which were measured during the topography measurement.

Patent Document 3 discloses a method of analyzing corneal topography of a cornea comprising the steps of: obtaining corneal curvature data; determining plural indexes characterizing topography of the cornea based on the obtained corneal curvature data; and judging corneal topography from features inherent in predetermined classifications of corneal topography using the determined indexes and a neural network so as to judge at least one of normal cornea, myopic refractive surgery, hyperopic refractive surgery, corneal astigmatism, penetrating keratoplasty, keratoconus, keratoconus suspect, pellucid marginal degeneration, or other classification of corneal topography.

CITATION LIST

Patent Literatures

Patent Document 1: US 2010/0060854 A1 equivalent to JP 2010-57897 A.
Patent Document 2: US 2013/0329187 A1 equivalent to JP 2013-255791 A.
Patent Document 3: US 2005/0225724 A1 equivalent to JP 2005-288176 A.

Non-Patent Literatures

Non-Patent Document 1: Rabinowitz Y S. Keratoconus. Sury Ophthalmol 1998; 42:297-319.
NON-PATENT DOCUMENT 2: de Sanctis U, Loiacono C, Richiardi L, Turco D, Mutani B, Grignolo F M. Sensitivity and specificity of posterior corneal elevation measured by Pentacam in discriminating keratoconus/subclinical keratoconus. Ophthalmology 2008; 115:1534-1539.
Non-Patent Document 3: Gordon-Shaag A, Millodot M, Ifrah R, Shneor E. Aberrations and topography in normal, keratoconus-suspect, and keratoconic eyes. Optom Vis Sci 2012; 89:411-418.

Non-Patent Document 4: Maeda N, Klyce S D, Smolek M K, Thompson H W. Automated keratoconus screening with corneal topography analysis. Invest Ophthalmol Vis Sci 1994; 35:2749-2757.

Non-Patent Document 5: Smolek M K, Klyce S D. Current keratoconus detection methods compared with a neural network approach. Invest Ophthalmol Vis Sci 1997; 38:2290-2299.

Non-Patent Document 6: Chastang P J, Borderie V M, Carvajal-Gonzalez S, Rostene W, Laroche L. Automated keratoconus detection using the EyeSys videokeratoscope. J Cataract Refract Surg 2000; 26:675-683.

Non-Patent Document 7: Twa M D, Parthasarathy S, Roberts C, Mahmoud A M, Raasch T W, Bullimore M A. Automated decision tree classification of corneal shape. Optom Vis Sci 2005; 82:1038-1046.

Non-Patent Document 8: Ambrosio R, Jr., Alonso R S, Luz A, Coca Velarde L G. Corneal-thickness spatial profile and corneal-volume distribution: tomographic indices to detect keratoconus. J Cataract Refract Surg 2006; 32:1851-1859.

Non-Patent Document 9: Pinero D P, Alio J L, Aleson A, Escaf Vergara M, Miranda M. Corneal volume, pachymetry, and correlation of anterior and posterior corneal shape in subclinical and different stages of clinical keratoconus. J Cataract Refract Surg 2010; 36:814-825.

Non-Patent Document 10: Fernandez Perez J, Valero Marcos A, Martinez Pena F J. Early diagnosis of keratoconus: what difference is it making? Br J Ophthalmol 2014; 98:1465-1466.

Non-Patent Document 11: Brown S E, Simmasalam R, Antonova N, Gadaria N, Asbell P A. Progression in keratoconus and the effect of corneal cross-linking on progression. Eye Contact Lens 2014; 40:331-338.

Non-Patent Document 12: Spira C, Grigoryan A, Szentmary N, Seitz B, Langenbucher A, Eppig T. [Comparison of the specificity and sensitivity of various instrument-guided keratoconus indices and classifiers]. Ophthalmologe 2015; 112:353-358.

Non-Patent Document 13: Shalek A K, Satija R, Adiconis X, Gertner R S, Gaublomme J T, Raychowdhury R, et al. Single-cell transcriptomics reveals bimodality in expression and splicing in immune cells. Nature. 2013; 498 (7453):236-40. doi: 10.1038/nature12172. PubMed PMID: 23685454; PubMed Central PMCID: PMCPMC3683364.

Non-Patent Document 14: Laurens van der Maaten G H. Visualizing Data using t-SNE. J Mach Learn Res 2008; 9:2579-2605.

Non-Patent Document 15: Rocha L M, Cappabianco F A M, Falcão A X. Data clustering as an optimum-path forest problem with applications in image analysis. International Journal of Imaging Systems and Technology. 2009; 19(2): 50-68. doi: doi:10.1002/ima.20191.

Non-Patent Document 16: Rehioui H, Idrissi A, Abourezq M, Zegrari F. DENCLUE-IM: A New Approach for Big Data Clustering. Procedia Computer Science. 2016; 83:560-7. doi: https://doi.org/10.1016/j.procs.2016.04.265.

Non-Patent Document 17: Yousefi S, Balasubramanian M, Goldbaum M H, Medeiros F A, Zangwill L M, Weinreb R N, et al. Unsupervised Gaussian Mixture-Model With Expectation Maximization for Detecting Glaucomatous Progression in Standard Automated Perimetry Visual Fields. Transl Vis Sci Technol. 2016; 5(3):2. doi: 10.1167/tvst.5.3.2. PubMed PMID: 27152250; PubMed Central PMCID: PMCPMC4855479.

Non-Patent Document 18: Yousefi S, Goldbaum M H, Balasubramanian M, Medeiros F A, Zangwill L M, Liebmann J M, et al. Learning from data: recognizing glaucomatous defect patterns and detecting progression from visual field measurements. IEEE Trans Biomed Eng. 2014; 61(7):2112-24. doi: 10.1109/TBME.2014.2314714. PubMed PMID: 24710816.

Non-Patent Document 19: Ankerst M, Breunig M M, Kriegel H-P, #246, Sander r. OPTICS: ordering points to identify the clustering structure. Proceedings of the 1999 ACM SIGMOD international conference on Management of data; Philadelphia, Pa., USA. 304187: ACM; 1999. p. 49-60.

Non-Patent Document 20: Zhao Y, Karypis G, Fayyad U. Hierarchical Clustering Algorithms for Document Datasets. Data Min Knowl Discov. 2005; 10(2):141-68. doi: 10.1007/s10618-005-0361-3.

Non-Patent Document 21: Martin Ester H-P K, Jörg Sander, Xiaowei Xu. A density-based algorithm for discovering clusters in large spatial databases with noise Knowledge discovery and data mining (KDD) 1996; 226-231.

Non-Patent Document 22: Li X, Yang H, Rabinowitz Y S. Keratoconus: classification scheme based on videokeratography and clinical signs. J Cataract Refract Surg 2009; 35:1597-1603.

Non-Patent Document 23: Saad A, Gatinel D. Topographic and tomographic properties of forme fruste keratoconus corneas. Invest Ophthalmol Vis Sci 2010; 51:5546-5555.

Non-Patent Document 24: Tomidokoro A, Oshika T, Amano S, Higaki S, Maeda N, Miyata K. Changes in anterior and posterior corneal curvatures in keratoconus. Ophthalmology 2000; 107:1328-1332.

Non-Patent Document 25: Holladay J T. Keratoconus detection using corneal topography. J Refract Surg 2009; 25:S958-962.

Non-Patent Document 26: Ambrosio R, Jr., Caiado A L, Guerra F P, et al. Novel pachymetric parameters based on corneal tomography for diagnosing keratoconus. J Refract Surg 2011; 27:753-758.

Non-Patent Document 27: Carvalho L A. Preliminary results of neural networks and zernike polynomials for classification of videokeratography maps. Optom Vis Sci 2005; 82:151-158.

Non-Patent Document 28: Arbelaez M C, Versaci F, Vestri G, Barboni P, Savini G. Use of a support vector machine for keratoconus and subclinical keratoconus detection by topographic and tomographic data. Ophthalmology 2012; 119:2231-2238.

Non-Patent Document 29: Smadja D, Touboul D, Cohen A, et al. Detection of subclinical keratoconus using an automated decision tree classification. Am J Ophthalmol 2013; 156:237-246 e231.

Non-Patent Document 30: Fernando Faria Correia I R, Bernardo Lopes, Marcella Q Salomão, Allan Luz, Rosane O Correa, Michael W Belin, Renato Ambrosio Jr. Topometric and Tomographic Indices for the Diagnosis of Keratoconus. International Journal of Keratoconus and Ectatic Corneal Diseases 2012; 1:92-99.

Non-Patent Document 31: Ruiz Hidalgo et al., Evaluation of a Machine-Learning Classifier for Keratoconus Detection Based on Scheimpflug Tomography, Cornea Vol 35, No. 6, June 2016, 827-832.

Non-Patent Document 32: Souza M B et al., Evaluation of machine learning classifiers in keratoconus detection from orbscan II examinations, CLINIC 2010; 65(12): 1223-1228.

SUMMARY OF THE INVENTION

Problem to be Resolved by the Invention

The object of the present invention is to provide a method for assisting corneal severity identification using unsupervised machine learning, or a method for identifying normal, disorder-suspect and disorder eyes by applying machine learning to a number of corneal tomography data.

Means for Solving the Problem

The invention is directed to a method for assisting corneal severity identification.

In one embodiment of the present invention, the method comprises: obtaining a corneal configuration data set of a cornea to be examined by a tomography; visualizing the corneal configuration data set of the cornea to be examined along with a number of pre-existing corneal configuration data sets of disorder corneas, disorder-suspect corneas and normal corneas obtained by the tomography using t-distributed Stochastic Neighbor Embedding in a two or three dimensional map, and judging corneal severity from the map.

In another embodiment of the present invention, the corneal severity is at least one selected from the group consisting of keratoconus severity, bullous keratopathy severity, walleye severity, keratoleukoma severity, keratohelcosis severity, herpes corneae severity, corneal chemical burn severity, corneal thermal burn severity, and degeneratio corneae severity.

In another embodiment of the present invention, the corneal configuration data set includes at least one of a 2D analysis of ACA viewing surface, a 2D analysis of CCT/ACD viewing surface, STAR360° (Scleral spur Tracking for Angle Analysis and Registration 360°), analysis of lens morphology on 2D Result, analysis of lens morphology on 3D Result, analysis of corneal morphology and reference points.

In another embodiment of the present invention, the 2D analysis of ACA viewing surface includes at least one of AOD500, AOD750, ARA500, ARA750, TISA500, TISA750, TIA500, and TIA750 (FIG. 6).

AOD500 (Angle Opening Distance 500) is a distance from AOD500-T to AOD500-IF (mm), wherein AOD500-T is a spot on trabecula (on Corneal inner surface) 500 μm away from SS(Scleral Spur), AOD500-IF is an intersection point of a line passing through AOD500-T and being vertical to a line joining SS and ARA-T with an anterior surface of iris, and ARA-T is a point on trabecula (on Corneal inner surface) 750 μm away from SS.

AOD750 (Angle Opening Distance 750 is a distance from ARA-T to ARA-IF (mm), wherein ARA-T is a point on trabecula (on Corneal inner surface) 750 μm away from SS and ARA-IF is an intersection point of a line passing through ARA-T and being vertical to a line joining SS and ARA-T with an anterior surface of iris.

ARA500 (Angle Recess Area 500) is a square measure of a region of angle recess bounded by a line joining AOD500-T and AOD500-IF ($mm^2$).

ARA750 (Angle Recess Area 750) is a square measure of a region of angle recess bounded by a line joining ARA-T and ARA-IF ($mm^2$).

TISA500 (Trabecular Iris Space Area 500) is a square measure of a region of angle recess bounded by a line joining SS and SS-IF and a line joining AOD500-T and AOD500-IF ($mm^2$), wherein SS-IF is an intersection point of a line passing through SS and being vertical to a line joining SS and ARA-T with an anterior surface of iris.

TISA750 (Trabecular Iris Space Area 750) is a square measure of a region of angle recess bounded by a line joining SS and SS-IF and a line joining ARA-T and ARA-IF ($mm^2$).

TIA500 (Trabecular-Iris Angle 500) is an angle between a line joining AR and AOD500-T and a line joining AR and AOD500-IF)(°, wherein AR is Angle Recess.

TIA750 (Trabecular-Iris Angle 750) is an angle between a line joining AR and ARA-T and a line joining AR and ARA-IF (°).

In another embodiment of the present invention, the 2D analysis of CCT/ACD viewing surface includes at least one of CCT, ACD Endo., LV, ACW, CCT, ACD[Epi.], ACD [Endo.], Vault, CLR and ATA.

CCT (Central Corneal Thickness) is a corneal thickness in intersection of a perpendicular bisector of a line segment (ACW) joining scleral spurs (SSs) with cornea (μm).

ACD Endo. (Anterior Chamber Depth Endothelium) is a depth of the anterior chamber from facies posterior corneae to facies anterior lentis (mm).

LV (Lens Vault) is a distance between facies anterior lentis on a perpendicular bisector of a line segment (ACW) joining scleral spurs (SSs) and perpendicular bisection point of ACW (mm).

ACW (Anterior Chamber Width) is a distance between scleral spurs (SSs) (mm).

CCT (Central Corneal Thickness) is a corneal thickness in intersection of a perpendicular bisector of a line segment joining angle recesses (ARs) with cornea (μm).

ACD[Epi.] (Anterior Chamber Depth [Epithelium]) is a depth of the anterior chamber from facies anterior corneae to facies anterior lentis (mm).

ACD[Endo.] (Anterior Chamber Depth [Endothelium]) is a depth of the anterior chamber from facies posterior corneae to facies anterior lentis (mm).

Vault (Vault) is a distance from facies posterior phakic (IOL) to facies anterior lentis (μm).

CLR (Crystalline Lens Rise) is a distance between facies anterior lentis on a perpendicular bisector of a line segment (ATA) joining angle recesses (ARs) and perpendicular bisection point of ATA (μm).

ATA (Angle to Angle) is a distance between angle recesses (ARs) (mm).

In another embodiment of the present invention, the STAR360° (Scleral spur Tracking for Angle Analysis and Registration 360°) includes at least one of AOD250, AOD500, AOD750, ARA250, ARA500, ARA750, TISA250, TIA500, TIA750, CCT, ACD Endo., LV, ACW, AC.Area, IT750, IT2000, I-Curv. and ITC.

AOD250 (Angle Opening Distance 250) is a distance from AOD250-T to AOD250-IF (mm), wherein AOD250-T is a spot on trabecula (on Corneal inner surface) 250 μm away from SS(Scleral Spur), AOD250-IF is an intersection point of a line passing through AOD250-T and being vertical to a line joining SS and ARA-T with an anterior surface of iris, and ARA-T is a point on trabecula (on Corneal inner surface) 750 μm away from SS.

AOD500 (Angle Opening Distance 500) is a distance from AOD500-T to AOD500-IF (mm), wherein AOD500-T is a point on trabecula (on Corneal inner surface) 500 μm away from SS and AOD500-IF is an intersection point of a line passing through AOD500-T and being vertical to a line joining SS and ARA-T with an anterior surface of iris, and ARA-T is a point on trabecula (on Corneal inner surface) 750 μm away from SS.

AOD750 (Angle Opening Distance 700) is a distance from ARA-T to ARA-IF (mm), wherein ARA-T is a point on trabecula (on Corneal inner surface) 750 μm away from SS and ARA-IF is an intersection point of a line passing through ARA-T and being vertical to a line joining SS and ARA-T with an anterior surface of iris.

ARA250 (Angle Recess Area 250) is a square measure of a region of angle recess bounded by a line joining AOD250-T and AOD250-IF (mm2).

ARA500 (Angle Recess Area 500) a square measure of a region of angle recess bounded by a line joining AOD500-T and AOD500-IF (mm2).

ARA750 (Angle Recess Area 750) a square measure of a region of angle recess bounded by a line joining ARA-T and ARA-IF (mm2).

TISA250 (Trabecular Iris Space Area 250) is a square measure of a region of angle recess bounded by a line joining SS and 55-IF and a line joining AOD250-T and AOD250-IF (mm2), wherein SS-IF is an intersection point of a line passing through SS and being vertical to a line joining SS and ARA-T with an anterior surface of iris.

TIA500 (Trabecular-Iris Angle 500) is an angle between a line joining AR and AOD500-T and a line joining AR and AOD500-IF (°), wherein AR is Angle Recess.

TIA750 (Trabecular-Iris Angle 750) an angle between a line joining AR and ARA-T and a line joining AR and ARA-IF)(°.

CCT (Central Corneal Thickness) is a corneal thickness in intersection of a perpendicular bisector of a line segment (ACW) joining scleral spurs (SSs) with cornea (μm).

ACD Endo. (Anterior Chamber Depth Endothelium) is a depth of the anterior chamber from facies posterior corneae to facies anterior lentis (mm).

LV (Lens Vault) is a distance between facies anterior lentis on a perpendicular bisector of a line segment (ACW) joining scleral spurs (SSs) and perpendicular bisection point of ACW (mm).

ACW (Anterior Chamber Width) is a distance between scleral spurs (SSs) (mm).

AC.Area (Anterior Chamber Area) is a square measure of Anterior Chamber (mm2).

IT750 (Iris Thickness 750) is an iris thickness at a position 750 μm away from SS (mm).

IT2000 (Iris Thickness 2000) an iris thickness at a position 2000 μm away from SS (mm).

I-Area (Iris Area) is a square measure of iris (mm2).

I-Curv. (Iris Curvatura) is a maximum of a distance from a line joining iris root (IR) and contact terminal of lens (IRT) to pigment epithelium (back side) of iris (mm).

ITC (Irido-Trabecular Contact) is contact of iris and trabecula.

In another embodiment of the present invention, the analysis of lens morphology on 2D Result includes at least one of Front R, Thickness, Diameter, Decentration and Tilt.

Front R (Front Radius) is a curvature radius of facies anterior lentis on 2D tomographic view (mm).

Back R (Back Radius) is a curvature radius of facies posterior lentis on 2D tomographic view (mm).

Thickness (Thickness) is a thickness of lens on 2D tomographic view (mm).

Diameter (Diameter) is an equatorial diameter of lens on 2D tomographic view (mm).

Decentration (Decentration) is an eccentric distance of a lens central axis from an axis (Vertex Normal) passing through apex of cornea on 2D tomographic view (mm).

Tilt (Tilt) is a tilt of lens center axis relative to an axis (Vertex Normal) passing through apex of cornea on 2D tomographic view (°).

In another embodiment of the present invention, the analysis of lens morphology on 3D Result includes at least one of Front R, Front Rs, Front Rf, Back R, Back Rs, Back Rf, Thickness, Diameter, Decentration, and Tilt.

Front R (Front Radius) is a mean of a steeper meridian Rs and a flatter meridian Rf of a curvature radius of facies anterior lentis on 3D (mm).

Front Rs (Front Radius Steep) is an axis angle (°) and a steeper meridian Rs (mm) of a curvature radius of facies anterior lentis on 3D.

Front Rf (Front Radius Flat) is an axis angle (°) and a flatter meridian Rf (mm) of a curvature radius of facies anterior lentis on 3D.

Back R (Back Radius) is a mean of a steeper meridian Rs and a flatter meridian Rf of a curvature radius of facies posterior lentis on 3D (mm).

Back Rs (Back Radius Steep) is an axis angle (°) and a steeper meridian Rs (mm) of a curvature radius of facies posterior lentis on 3D.

Back Rf (Back Radius Flat) is an axis angle (°) and a flatter meridian Rf (mm) of a curvature radius of facies posterior lentis on 3D.

Thickness (Thickness) is a thickness of lens on 3D (mm).

Diameter (Diameter) is an equatorial diameter of lens on 3D (mm).

Decentration (Decentration) is an axis angle (°) and an eccentric distance (mm) of a lens central axis from an axis (Vertex Normal) passing through apex of cornea on 3D.

Tilt (Tilt) is a tilt of lens center axis relative to an axis (Vertex Normal) passing through apex of cornea on 3D (°).

In another embodiment of the present invention, the analysis of corneal morphology includes at least one of Ks, Kf, CYL, ACCP, ECC, AA, Apex, Thinnest, and ESI.

Ks (Keratometry Steep) is a steeper meridian equivalent to K2 in Keratometer (D or mm).

Kf (Keratometry Flat) is a flatter meridian equivalent to K1 in Keratometer (D or mm).

CYL (Cylinder) is a corneal astigmatism (D).

ACCP (Average Central Corneal Power) is a mean of corneal refractive power within a 3 mm diameter (D).

ECC (Eccentricity) is a corneal eccentricity.

AA (Analyzed Area) is ratio of a region available to corneal morphology analysis (%).

Apex (Apex) is a thickness of corneal center in corneal thickness map (μm).

Thinnest (Thinnest) is a thickness of thinnest portion in corneal thickness map (μm).

ESI (Ectasia Screening Index) is an index for screening keratoconus.

In another embodiment of the present invention, the reference points includes at least one of SS, AR, IR, IRT, and EP.

SS is Scleral Spur, AR is Angle Recess, IR is Iris Root, IRT is Iris Rear Tip (contact terminal of lens), and EP is End Point (ITC terminal).

In another embodiment of the present invention, the corneal configuration data set includes at least one of DSI, OSI, CSI, SD_P (4 mm), CV_P (4 mm), ACP (3 mm), RMS_E (4 mm), SR_E (4 mm), SR_H (4 mm), CSI_T, SD_T (4 mm), and CV_T (4 mm).

As shown in FIG. 8, a φ9 region of a cornea is divided into 8 equal sectors. Differential Sector Index (DSI) is defined as a difference calculated by subtracting Min_Area_Power [D] from Max_Area_Power [D]. Opposite Sector Index (OSI) is defined as a difference calculated by subtracting Opposite_Area_Power [D] from Max_Area_Power [D], wherein Max_Area_Power [D] is defined as the highest refractive power (axial power). Min_Area_Power [D] is defined as the lowest refractive power (axial power).

$$DSI = \text{Max\_Area\_Power} - \text{Min\_Area\_Power [D]}$$

$$OSI = \text{Max\_Area\_Power} - \text{Opposite\_Area\_Power [D]}$$

Opposite_Area_Power [D] is defined a refractive power (axial power) in a sector located on opposite side of a sector having the highest refractive power (axial power).

Center Surround Index (CSI) is defined as a difference calculated by subtracting OuterP [D] from InnerP [D], wherein InnerP [D] is a refractive power (axial power) in center region (φ0-3 mm) and OuterP [D] is a refractive power (axial power) in a peripheral region (φ3-6 mm) as shown FIG. 9.

$$CSI = \text{Inner}P - \text{Outer}P\,[D]$$

Standard Deviation of corneal Power (φ4) (SD_P (4 mm)) is defined as a standard deviation of refractive power (axial power) data within a φ4 region of cornea calculated by the following formula.

$$\text{SD\_P(4 mm)} = \sqrt{\frac{\sum_{i=1}^{N}(P_i - \overline{P})^2}{N-1}} \quad [D]$$

N is number of refractive power (axial power) data, P is refractive power (axial power) data, and is an average of refractive power (axial power).

Coefficient of Variation of corneal Power (φ4) (CV_P (4 mm) is defined as a variation coefficient of refractive power (axial power) data within a φ4 region of cornea calculated by the following formula.

$$\text{CV\_P(4 mm)} = \frac{1000 \times \text{SD\_P(4 mm)}}{\overline{P}}$$

Average Corneal Power (φ3) (ACP (3 mm) is defined as an average of refractive power (axial power) data within a φ4 region of cornea calculated by the following formula. P(i) is a measuring point, PatchArea(i) is a square measurement of the measuring point (FIG. 10).

$$ACP(3 \text{ mm}) = \frac{\sum_{j=1}^{N}(PatchArea(i) \times P(i))}{\sum_{i=1}^{N} PatchArea(i)} \quad [D]$$

Root Mean Square of corneal Elevation (φ4) (RMS_E(4 mm)) is defined as a root mean square of Elevation data within a φ4 region of cornea calculated by the following formula.

$$\text{RMS\_E(4 mm)} = \sqrt{\frac{\sum_{i=1}^{N} E_i^2}{N}}$$

N is number of elevation data, and E is elevation data.

Surface Regularity of corneal Elevation (φ4) (SR_E(4 mm)) is defined as a surface regularity index (SRI) based on Elevation data within a φ4 region of cornea calculated by the following formula (FIG. 11).

$$f'''(i) = \frac{-E_1(i) + 3E_2(i) - 3E_3(i) + E_4(i)}{\Delta \text{Radius}} \quad (I)$$

$$\text{SR\_E} = 1000 * \sqrt{\frac{\sum_{i=1}^{N} f'''^2(i)}{N}} \quad (II)$$

$$f''(i) = \left| P_2(i) - \frac{P_1(i) + P_3(i)}{2} \right| \quad (III)$$

$$SRI = \ln(1000 * f''(i)) - 3.5 \quad (IV)$$

Surface Regularity of corneal Height (φ4) (SR_H(4 mm)) is defined as a Surface Regularity Index based on Height data within a φ4 region of cornea calculated by the following formula (FIG. 12).

$$f'''(i) = \frac{-H_1(i) + 3H_2(i) - 3H_3(i) + H_4(i)}{\Delta \text{Radius}} \quad (I)$$

$$\text{SR\_H} = 100 * \sqrt{\frac{\sum_{i=1}^{N}(PatchArea(i) \times f'''^2(i))}{\sum_{i=1}^{N} PatchArea(i)}} \quad (II)$$

Center Surround Index of Thickness (CSI_T) is defined as a difference between an average thickness of center region (φ3) and an average thickness of peripheral region (φ6) calculated by the following formula (FIG. 13).

$$CSI\_T = \text{Inner}T - \text{Outer}T \text{ [um]}$$

Standard Deviation of Thickness (φ4) (SD_T(4 mm)) is defined as a standard deviation of corneal thickness (Pachymetry) within a φ4 region of cornea calculated by the following formula.

$$\text{SD\_T(4 mm)} = \sqrt{\frac{\sum_{i=1}^{N}(T_i - \overline{T})^2}{N-1}} \quad [D]$$

Coefficient of Variation of Thickness (φ4) (CV_T(4 mm)) is defined as a variation coefficient of corneal thickness (Pachymetry) within a φ4 region of cornea calculated by the following formula.

$$\text{CV\_T(4 mm)} = \frac{1000 \times \text{SD\_T(4 mm)}}{\overline{T}}$$

In another embodiment of the present invention, the tomography is an optical coherence tomography.

In another embodiment of the present invention, the optical coherence tomography is an anterior eye part optical coherence tomography.

In another embodiment of the present invention, the optical coherence tomography is a swept-source optical coherence tomography.

Advantageous Effects of the Invention

The proposed method identified four clusters; I: a cluster composed of mostly normal eyes (224 eyes with ESI equal to zero, 23 eyes with ESI between five and 29, and nine eyes with ESI greater than 29), II: a cluster composed of mostly healthy eyes and eyes with forme fruste keratoconus (1772 eyes with ESI equal to zero, 698 eyes with ESI between five and 29, and 117 eyes with ESI greater than 29), III: a cluster composed of mostly eyes with mild keratoconus stage (184 eyes with ESI greater than 29, 74 eyes with ESI between five and 29, and 6 eyes with ESI equal to zero), and IV: a cluster composed of eyes with mostly advanced keratoconus stage (80 eyes had ESI greater than 29 and 1 eye had ESI between five and 29). We found that keratoconus status and severity can be well identified using unsupervised machine learning algorithms along with linear and non-linear corneal data transformation. The proposed method can better identify and visualize the corneal disease stages.

EMBODIMENTS FOR CARRYING OUT THE INVENTION

Figure 1:
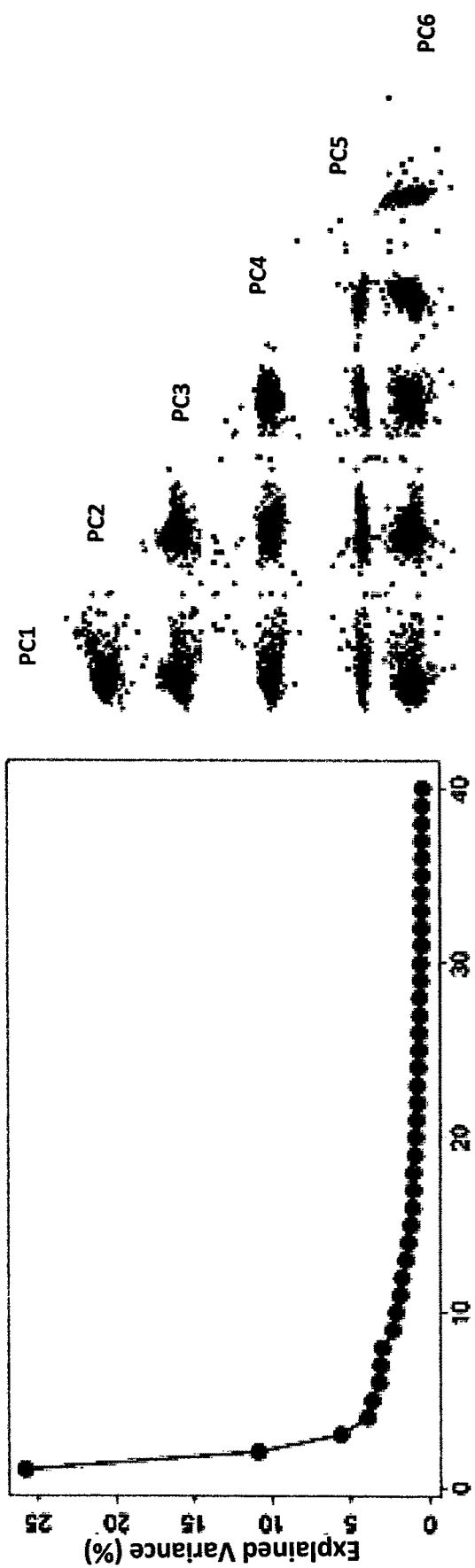
FIG. 1 Applying principal component analysis on corneal features. Left: explained variance of the first 40 significant principal components. Right: corneal features in the space of the first six principal components.

In this multi-center retrospective study, we collected corneal optical coherence tomography (OCT) images from 12,242 eyes of 3162 subjects using SS-1000 CASIA OCT Imaging Systems (Tomey, Japan) and other parameters from the electronic health record (EHR) system. All data available at each instrument was collected without any pre-condition. We then selected a single visit from each eye and excluded eyes with missing Ectasia Status Index (ESI). A total of 3,156 eyes met the criterion. About 57% of the participants were female and the mean age was 69.7 (standard deviation; SD=16.2) years. Three screening labels were derived from the ESI index of Casia (produced by TOMEY Corporation); normal if ESI is between 0 and 4, forme fruste keratoconus (or keratoconus-suspect) if ESI is between 5 and 29, and keratoconus if ESI is 30 or greater. Using Casia labels, our dataset included 1970 healthy eyes, 796 eyes with forme fruste keratoconus, and 390 eyes with keratoconus. ESI is basically an instrument-guided screening index which has been shown to have a good agreement with Belin-Ambrosio (BA) index in diagnosing keratoconus (Non-Patent Document 12). This study was performed in accordance with the ethical standards in the Declaration of Helsinki and institutional review board (IRB) was submitted and approved in the "Jichi Medical University IRB Office. Data use agreement was signed between centers in Japan and our institute to conduct the analysis. The data was de-identified in Japan before any further processing.

Four hundred and twenty parameters including axial, refractive, elevation, and pachymetry of both anterior and posterior surfaces of cornea were selected for the unsupervised machine learning analysis. All ESI-related parameters were excluded from the dataset. We first applied a principal component analysis (PCA) using prcomp function in the R package to the 420 selected corneal parameters. PCA uses a linear and orthogonal transformation to convert the observations of highly correlated corneal parameters into a set of new parameters which are linearly uncorrelated to each other. In another word, each new principal component parameter is a weighted combination of all initial corneal parameters while the components do not carry correlation anymore. This transformation allowed us to linearly reduce the number of dimensions of the original dataset. To investigate how many principal components are significant compared to a generated null distribution, we generated 100 independent artificial datasets such that within each dataset, the values along every corneal parameter were randomly permuted (Non-Patent Document 13). This operation removes the pairwise correlations between corneal parameters while keeping the distribution of every parameter unchanged. We then applied PCA to each of these 100 artificial VF datasets and sorted the combined eigenvalues of different datasets. We identified the principal components in our dataset in which their eigenvalues were significantly greater than the top eigenvalues from the artificial datasets ($p<0.01$, Bonferroni corrected).

We then applied manifold learning using t-distributed stochastic neighbor embedding (tSNE) (see Non-Patent Document 14) to group eyes with similar corneal characteristic together and to separate eyes with dissimilar characteristics as far away as possible. We used Rtsne function in the R package for this purpose. This process maps eyes with similar local distance metrics in the tSNE space and nonlinearly reduce the dimension of input data. Moreover, tSNE is well-suited for visualization and monitoring the progress of the disease by clinicians since it provides a user-friendly visualization. Moreover, it allows subjective validation of the follow-up unsupervised clustering because one can see how the clusters are distributed and overlapped in 2- or 3-dimensional space. More importantly, tSNE generates more distinct and non-overlapping clusters compared to the best two principal components.

While there are several unsupervised clustering algorithms for identifying hidden structures in datasets (Non- Patent Documents 15-20), we employed an unsupervised density-based clustering (see Non-Patent Document 21) in the tSNE space to identify eyes with similar corneal characteristics in tSNE space and to group the eyes into non-overlapping clusters objectively. Density-based clustering groups eyes in the tSNE space that that are closely packed together and have many neighbors around them while eyes that lie alone (in low-density areas) and are too far away will be marked as outlies and not members of groups. We then assessed the accuracy of the approach both qualitatively (visualization) and quantitatively (using screening index of the Casia instrument).

FIG. 1 (left) shows the top 40 principal components and the amount of variance in data explained by those components. We identified 32 principal components as significant based on our quantitative analysis. The top 32 principal components explained over 80% of the total variability in the data while the top eight principal components carried approximately 60% of the total variability in the data. However, after investigating tSNE maps, we selected 8 principal components which showed a more discriminative clusters on the tSNE map (qualitative validation). We generated two corneal eigen-parameters which is essentially a nonlinear combination of original corneal parameters.

Figure 2:
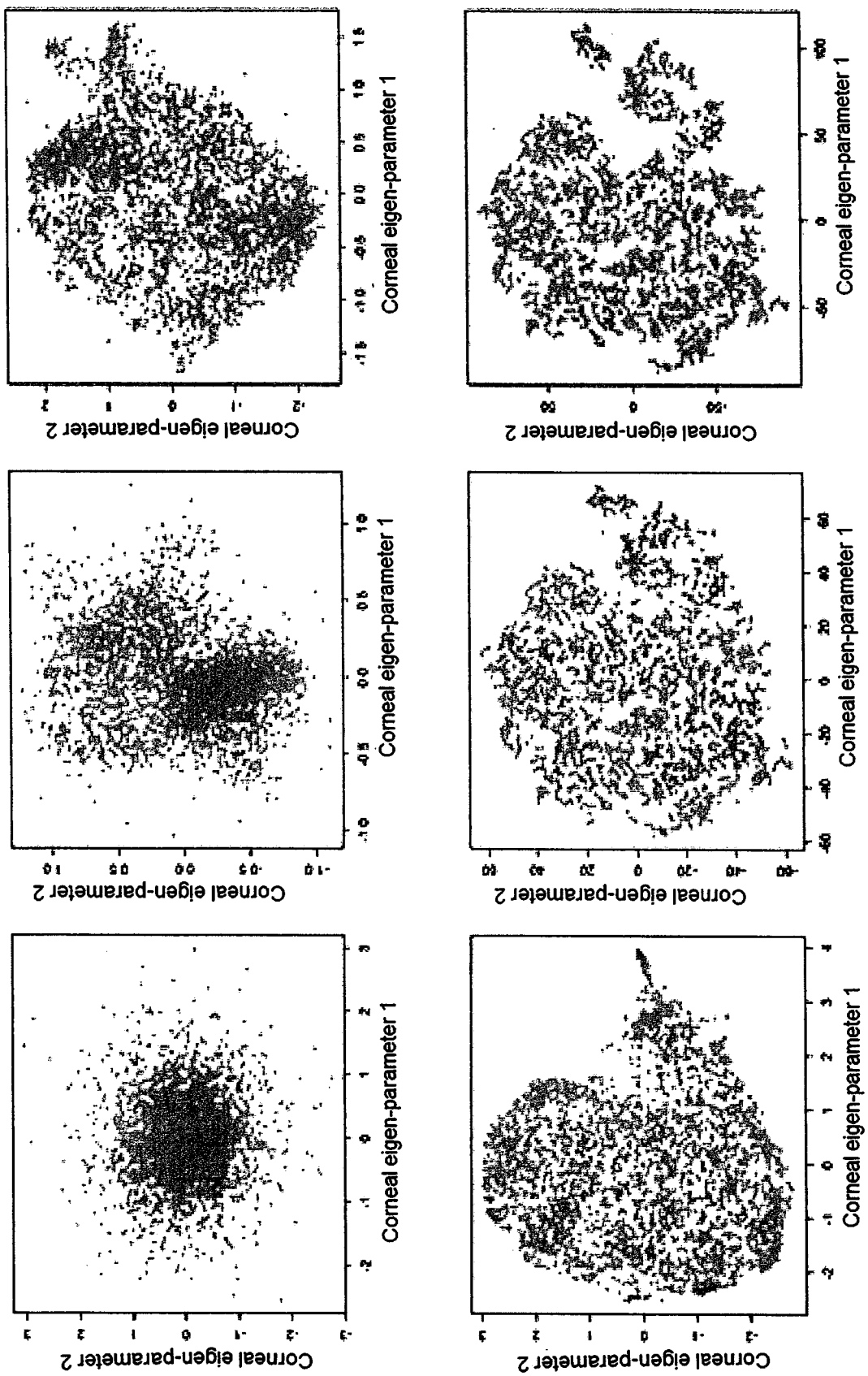
FIG. 2 Evolution of corneal parameters in 2-D tSNE space. Zigzag, left to right, shows the evolution of tSNE over time starting from initial state which the corneal parameters are simply collapsed onto a 2-D space and then grouping eyes with similar corneal characteristics together over time.

FIG. 2 shows the evolution of tSNE over time starting from the initial state in which the corneal parameters are collapsed in 2-D space without considering the local characteristics among points. We selected 2-D because it provides a user-friendly, importantly, a clinician-friendly visualization. The algorithm then identifies eyes with similar characteristics based on their distances in the tSNE space and gradually groups them together. The perplexity which reflects the assumed number for the neighbors for each point was set to 34 and we allowed the maximum number of iterations to 1000.

Figure 3:
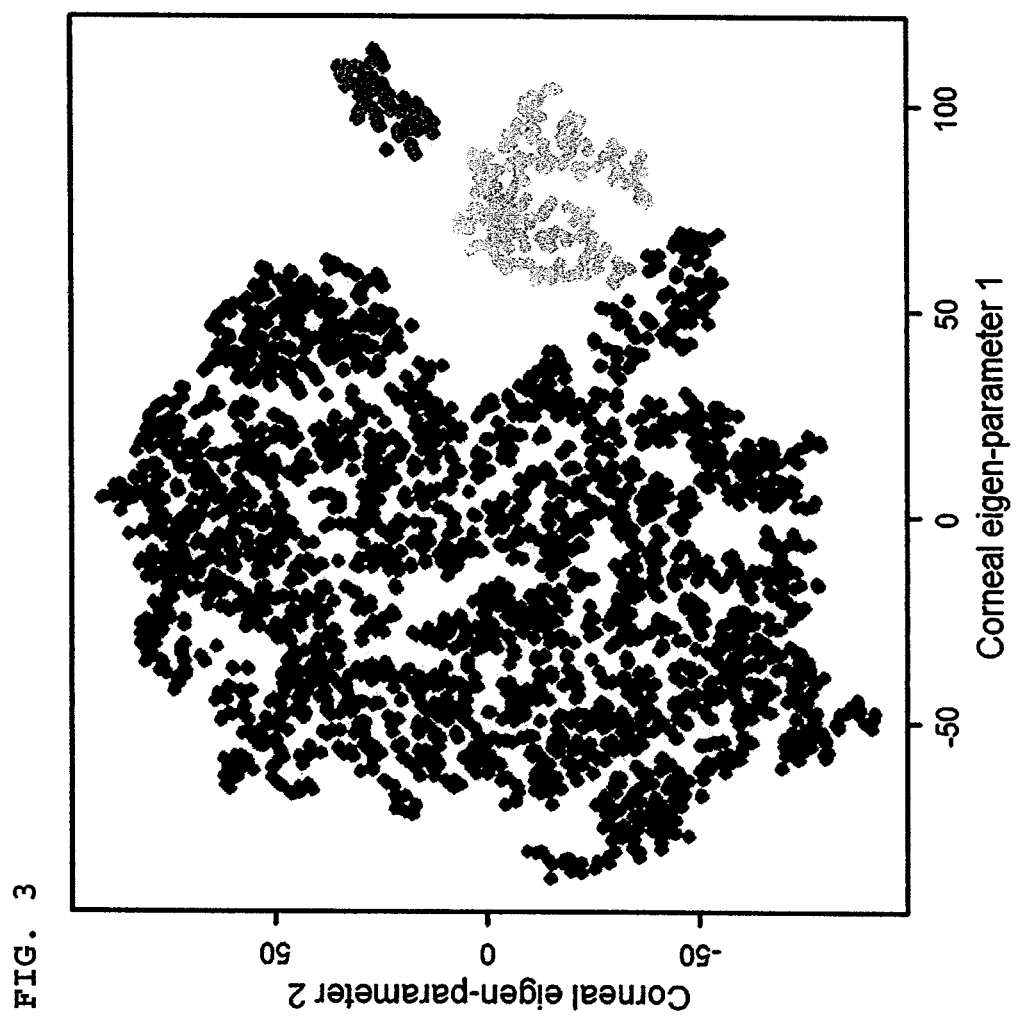
FIG. 3 Unsupervised machine learning identified four clusters of eyes with similar corneal characteristics.

To subjectively assess the accuracy of learning, we applied unsupervised density-based clustering on the two identified corneal eigen-parameters. Clusters with fewer than seven eyes were excluded. Unsupervised density-based clustering identified four non-overlapping clusters. For a better visualization, we color-coded the clusters as shown in FIG. 3.

We then assigned clinical labels to the four identified clusters based on the ESI index (ranging from 0 to 100) provided by Casia instrument, where zero indicates normal and 100 reflects the most advanced stage of keratoconus. Casia instrument also provides diagnostic labels based on the ESI index: normal if ESI equals to zero, forme fruste keratoconus (or keratoconus-suspect) if ESI is between 5 and 29, and keratoconus if ESI is greater than 29. However, it is unclear how this index is generated from all corneal parameters and, more importantly, how the threshold for identifying eyes with forme fruste keratoconus is identified. Moreover, the currently used forme fruste keratoconus threshold index is confusing by its nature since keratoconus represents a spectrum of corneal deformations particularly in the early stages of the disease and it is challenging to assign a binary label to segregate a normal eye from an eye with forme fruste keratoconus. Nevertheless, using the Casia ESI index and diagnostic labeling convention, we determined that cluster I (color-coded black) was mainly composed of healthy eyes: 224 healthy eyes, 23 eyes with forme fruste keratoconus, and nine eyes with keratoconus. Cluster II (color-coded gray—big cluster on the left) was mainly composed of healthy eyes and eyes with forme fruste keratoconus: 1772 healthy eyes, 698 eyes with forme fruste keratoconus, and 117 eyes with keratoconus. Cluster III (color-coded light gray) was mostly composed of eyes with mild keratoconus: 184 eyes with mild keratoconus, 74 eyes with forme fruste keratoconus, and six healthy eyes. The small cluster IV (color-coded white-triangular black) was mainly composed of eyes with advanced keratoconus: 80 eyes with advanced keratoconus and one eye with forme-fruste keratoconus.

Figure 4:
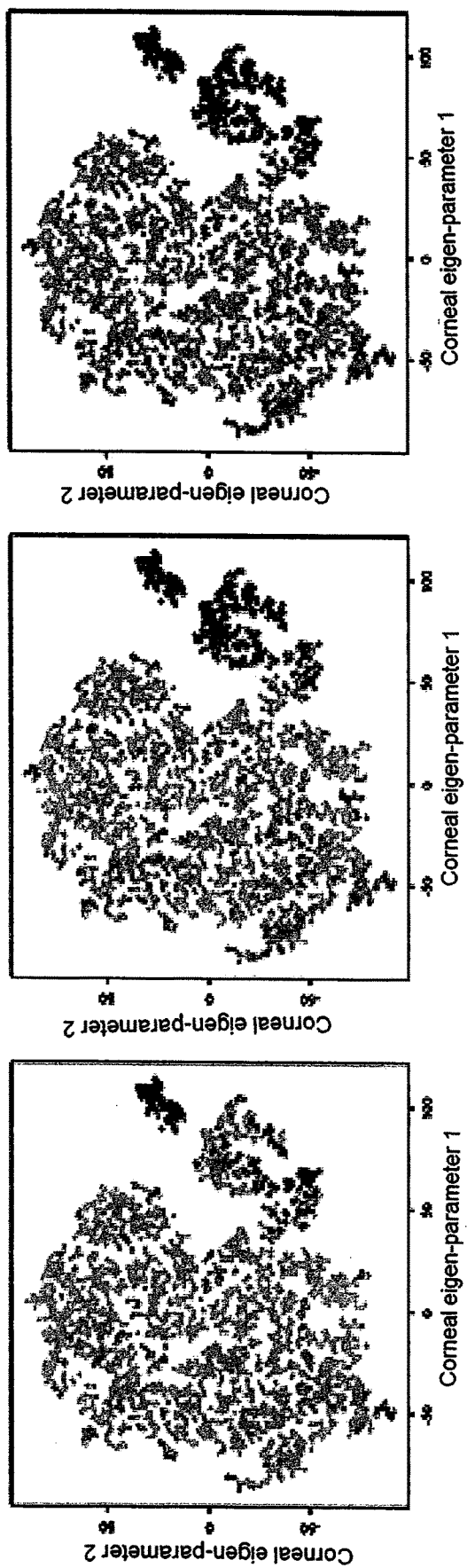
FIG. 4 Mapping ESI index on clustering. Left: ESI index corresponding to anterior segment of cornea, Middle: ESI index corresponding to posterior segment of cornea, and Right: overall ESI index of Casia instrument.

To subjectively evaluate the correlation between the severity of keratoconus of eyes in the identified clusters and the ESI index of the Casia instrument, we color-coded each eye on the clustering plot with anterior, posterior, and total ESI indices reflecting the severity of keratoconus. FIG. 4 shows the mapping of anterior, posterior, and total ESI indices onto the clusters we identified.

To objectively assess the accuracy of unsupervised clustering, we computed the specificity and sensitivity based on Casia diagnostic labeling. The specificity of identifying healthy eyes from eyes with keratoconus was 94.1% and the sensitivity of identifying eyes with keratoconus from healthy eyes was 97.7%.

Figure 5:
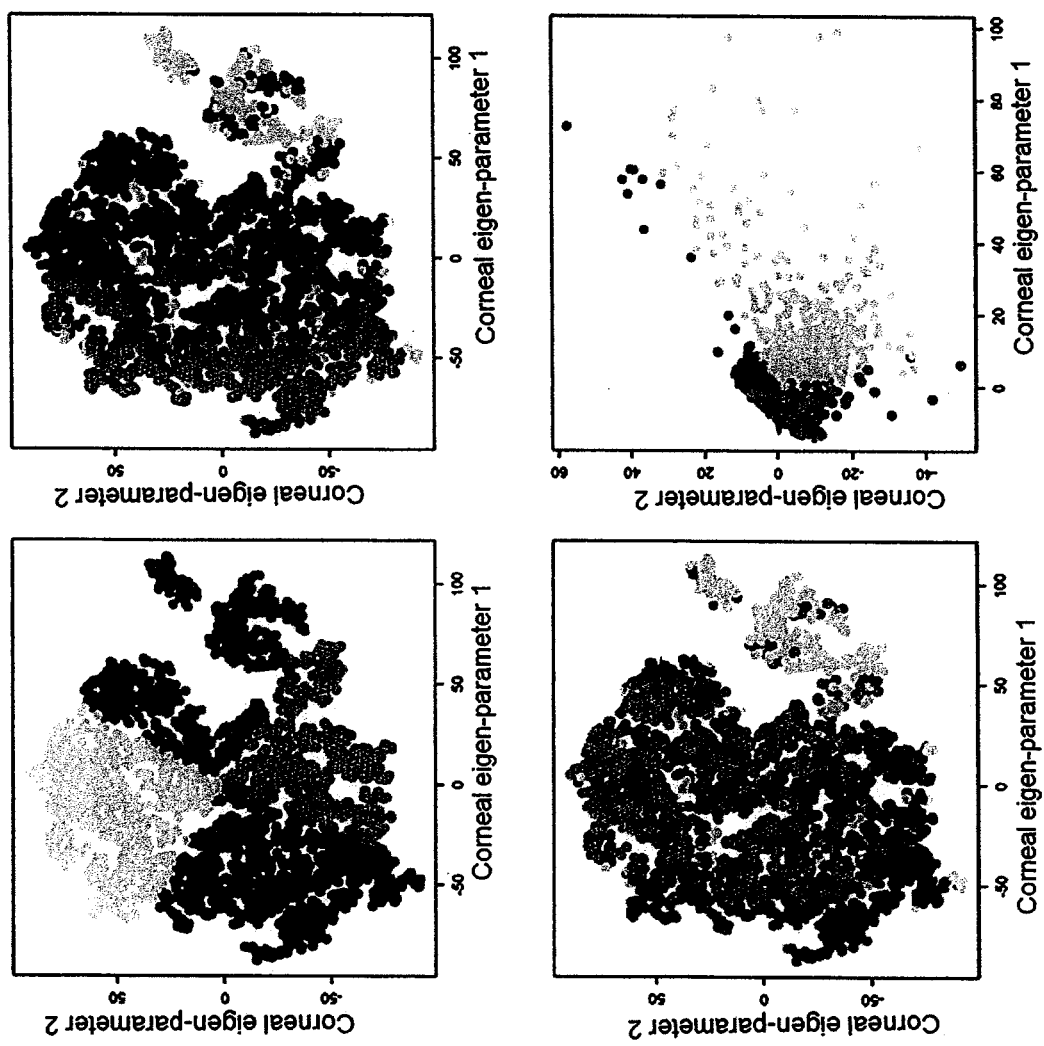
FIG. 5 Investigating CLUTO, another density-based clustering algorithm. Top left: CLUTO was applied on the tSNE eigen-parameters and visualized on the tSNE map, Top right: CLUTO was applied on the PCA components and visualized on the tSNE map, Bottom left: CLUTO was applied on the original data with 420 parameters and visualized on the tSNE map, Bottom right: CLUTO was applied on the original data and visualized using two significant principal components.
Figure 6:
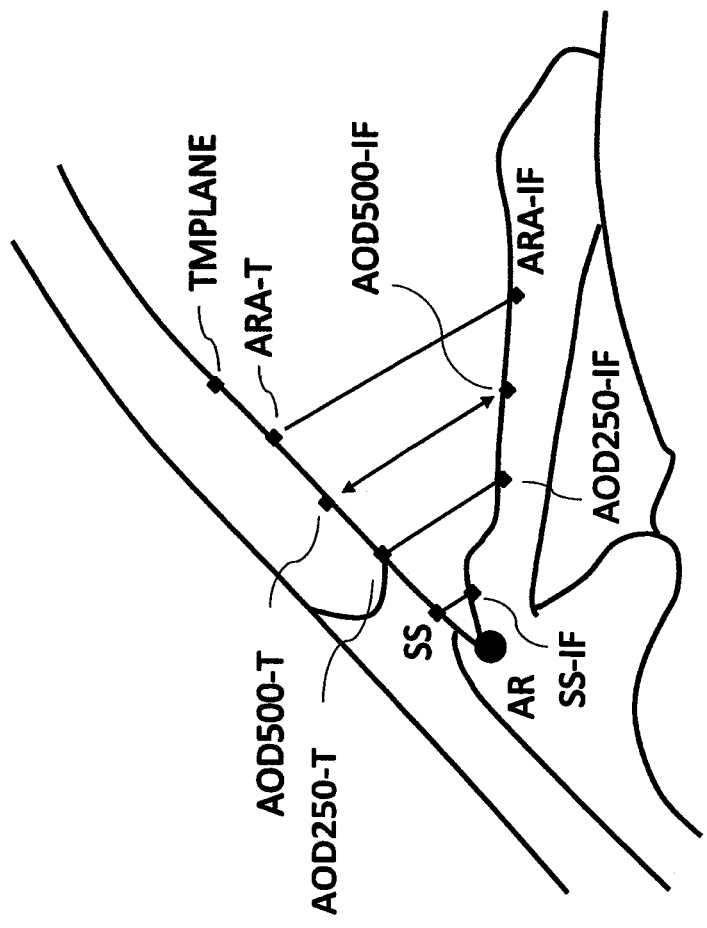
FIG. 6 A diagram showing a concept of 2D analysis.
Figure 7:
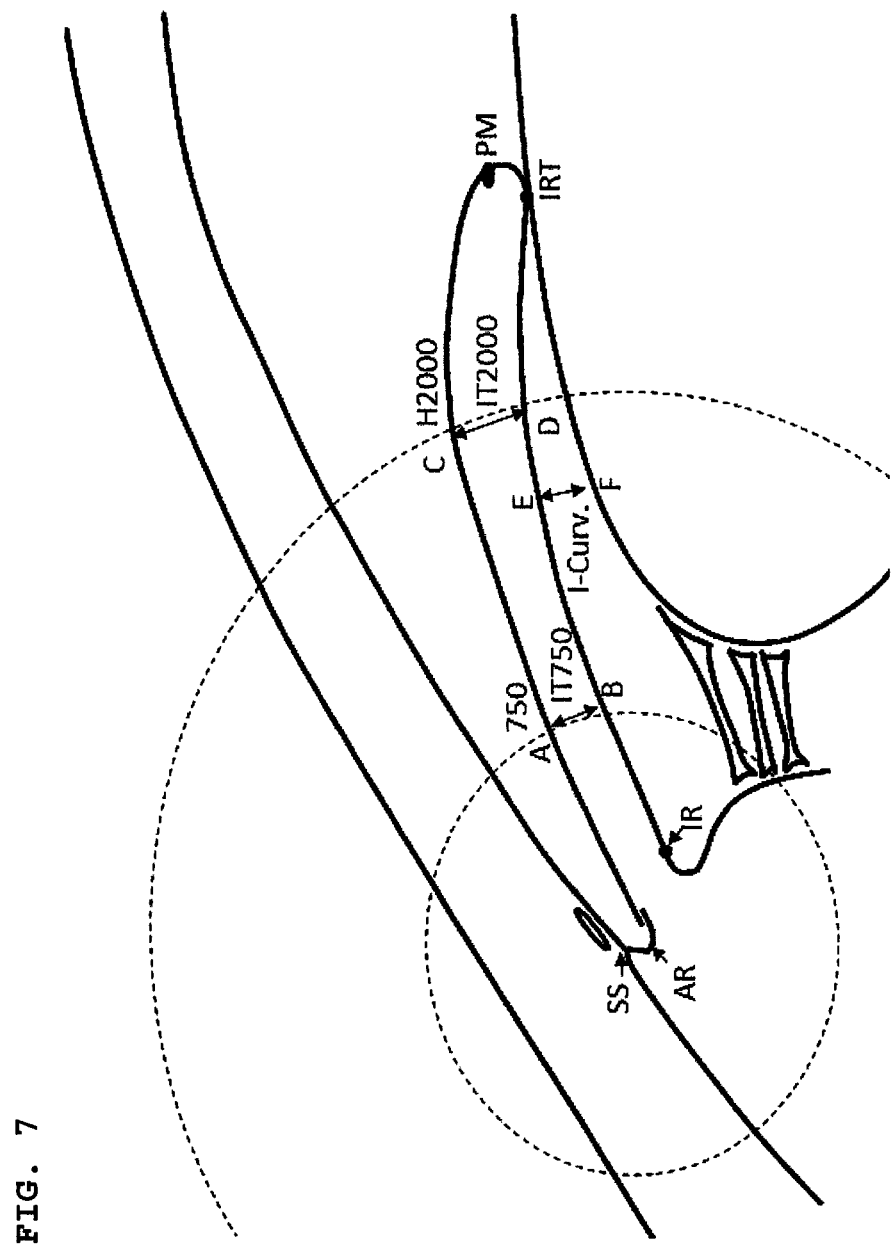
FIG. 7 A diagram showing a concept of STAR360° 2D analysis.
Figure 8:
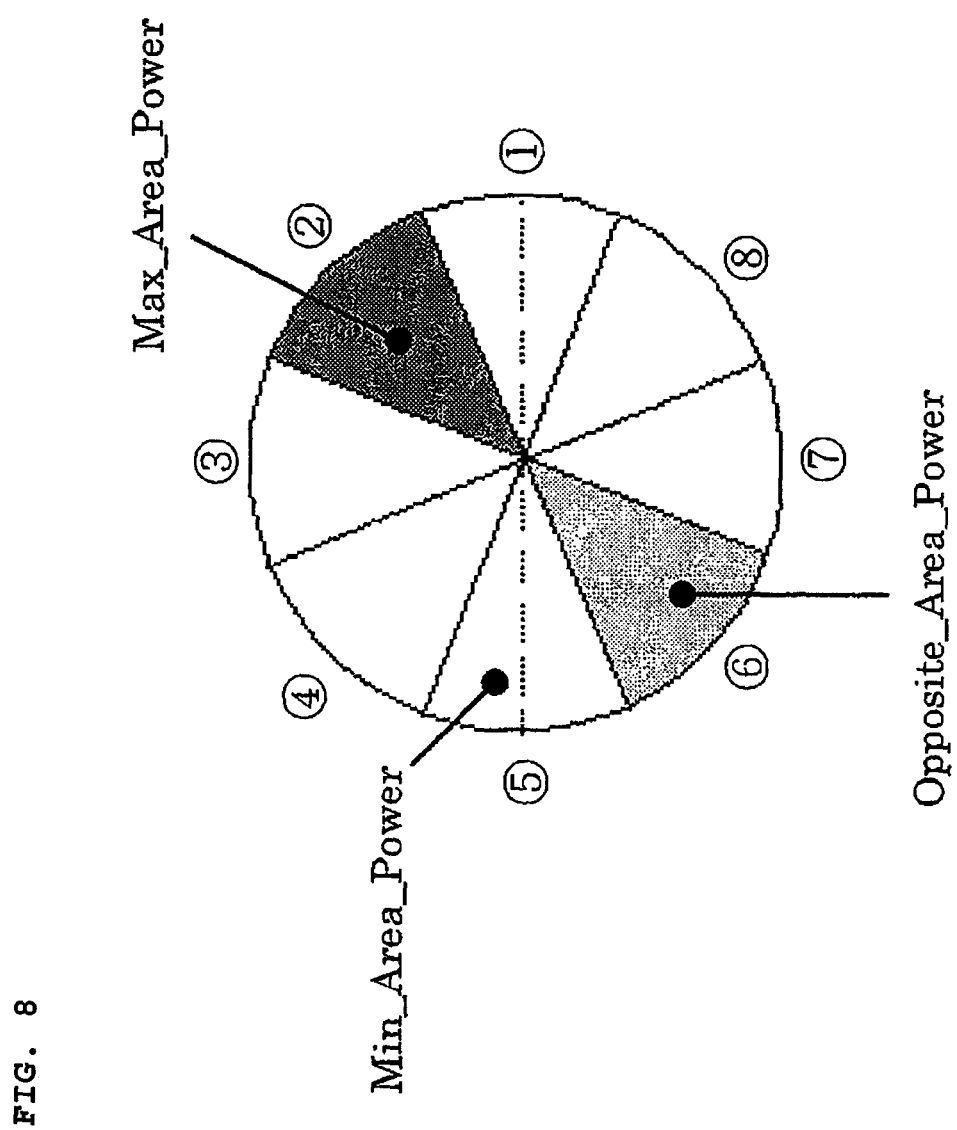
FIG. 8 A diagram showing a φ9 region of a cornea divided into 8 equal sectors.
Figure 9:
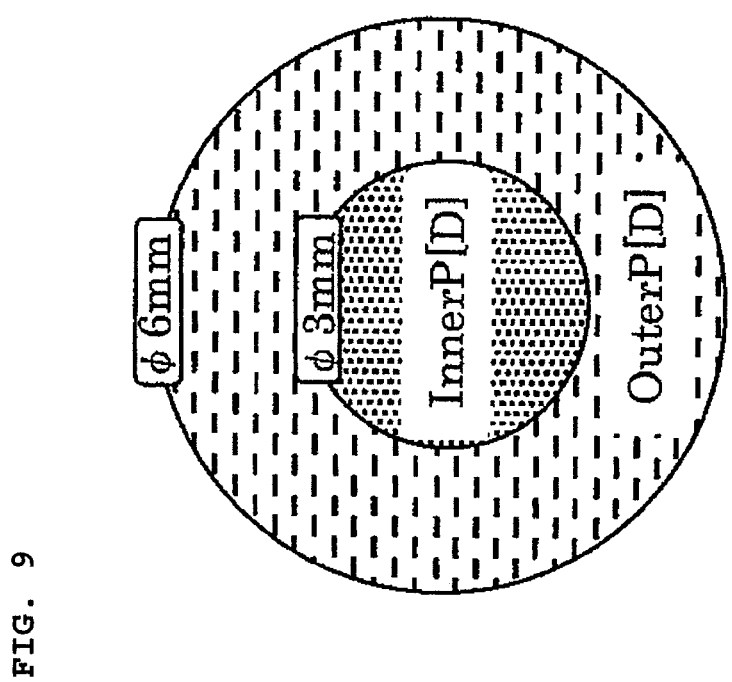
FIG. 9 A diagram showing a concept of CSI.
Figure 10:
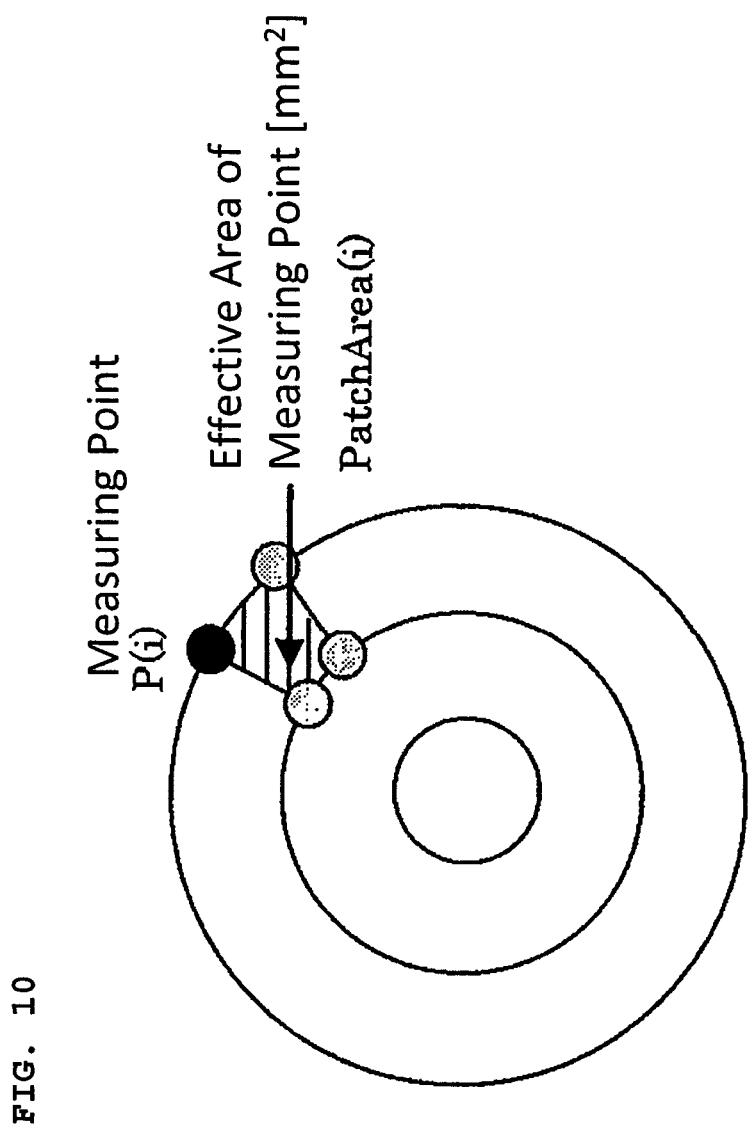
FIG. 10 A diagram showing a concept of measuring point.
Figure 11:
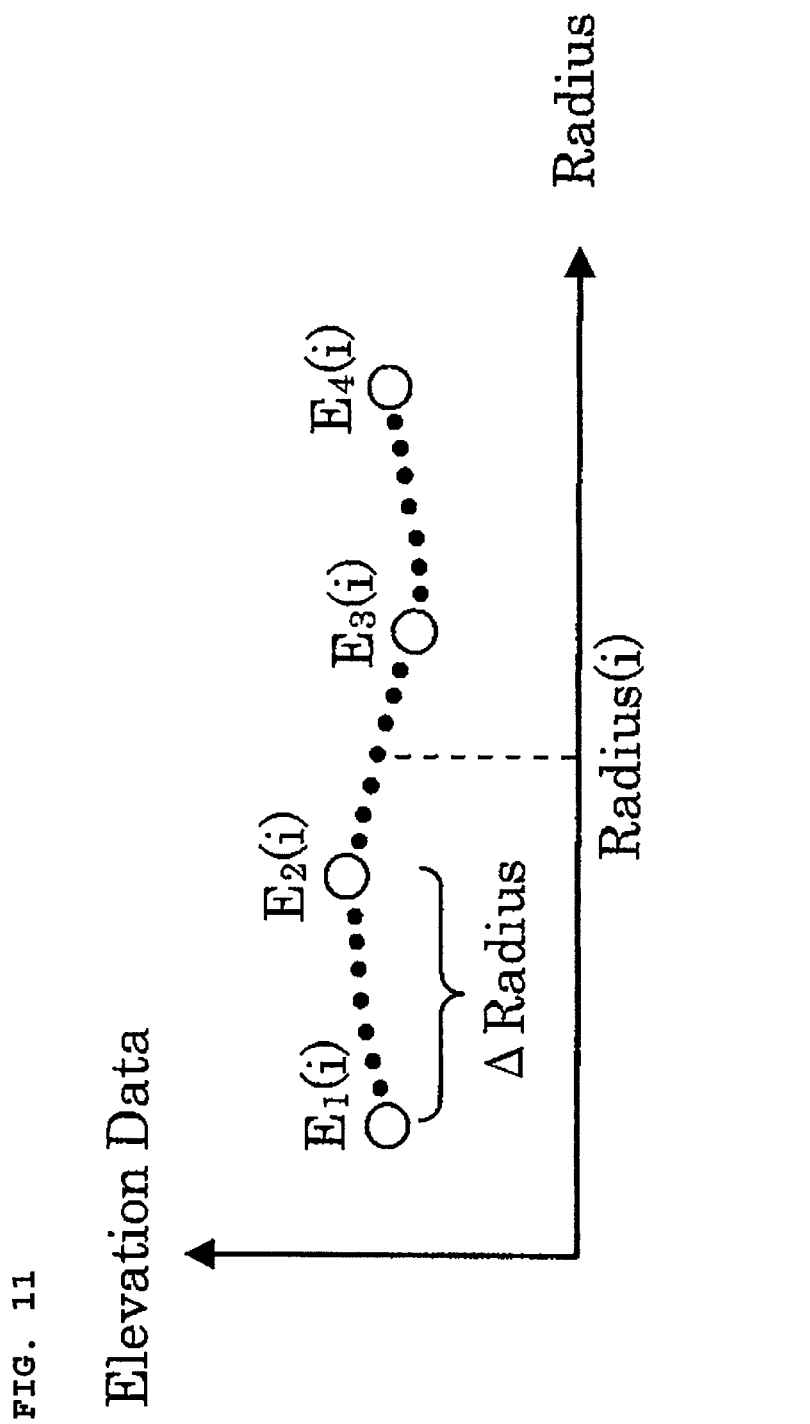
FIG. 11 A diagram showing a concept of Elevation.
Figure 12:
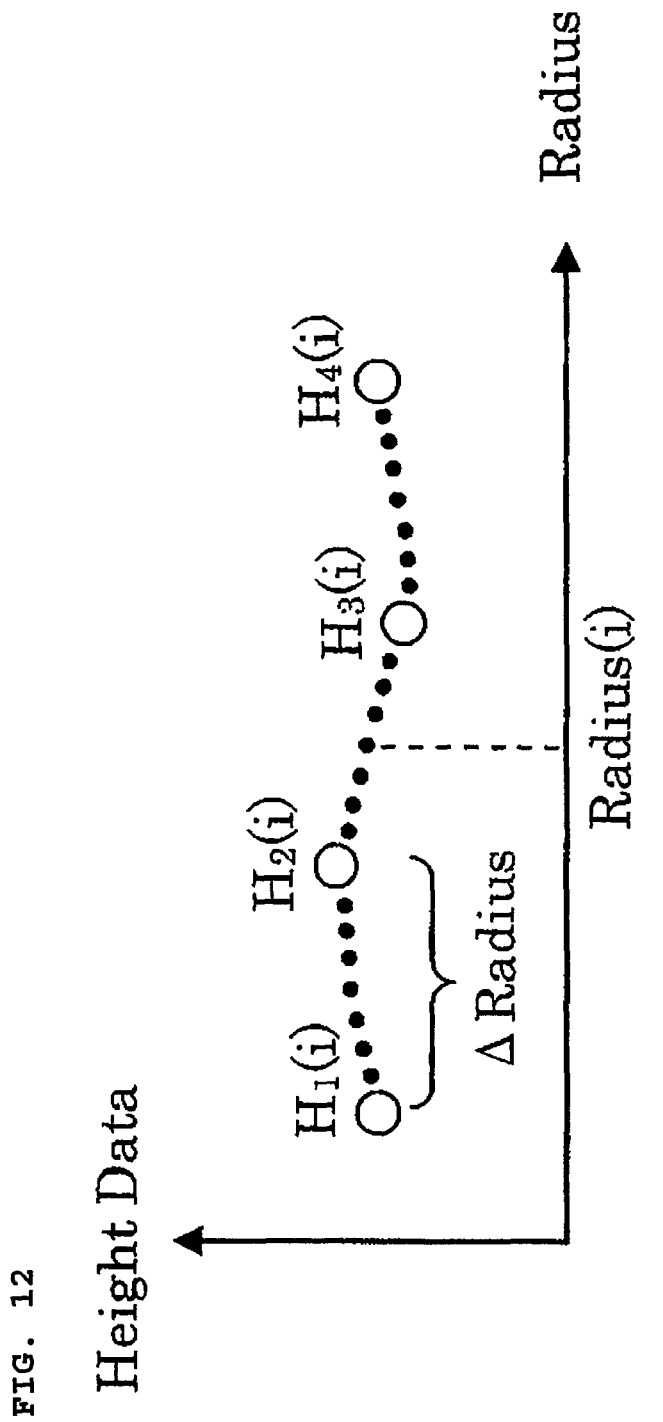
FIG. 12 A diagram showing a concept of Height.
Figure 13:
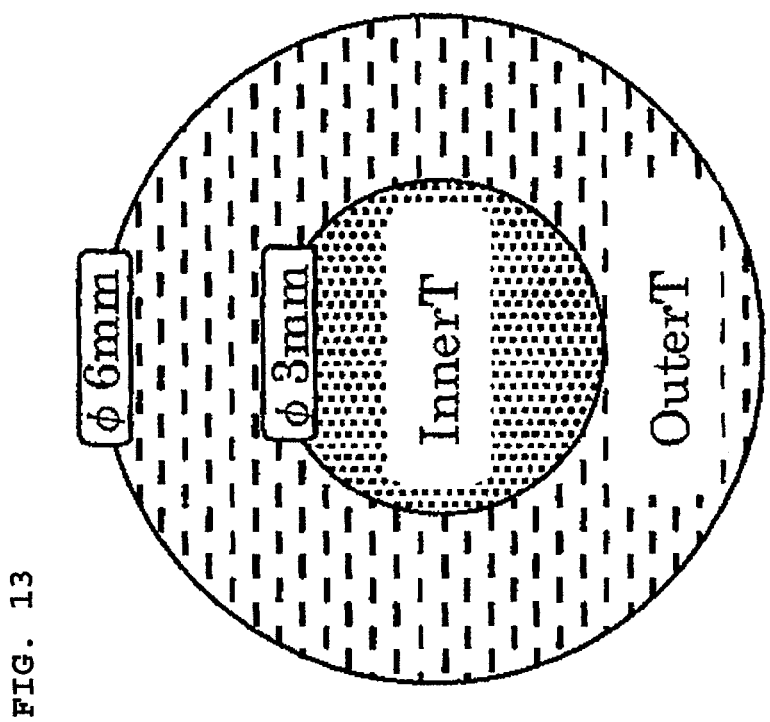
FIG. 13 A diagram showing a concept of CSI_T.

To compare the DBSCAN clustering algorithm to other approaches, we investigated the OPTICS (Non-Patent Document 19] and the Clustering Toolkit (CLUTO) algorithm (Non-Patent Document 20). CLUTO is a software package for unsupervised clustering of low- and high-dimensional datasets. We first applied CLUTO on the tSNE and visualized the outcome. We then asked whether CLUTO generates more discriminant clusters using principal components or the original data with 420 parameters. FIG. 5 shows how CLUTO clustered the eyes using tSNE eigen-parameters, principal components, and original data. As can be seen, none of the outcomes generated a well-separated clusters. To assess the outcome of clustering objectively, we further investigated the specificity and sensitivity of the clusters using the same approach that we performed for DBSCAN. We determined that DNCLUE generates four clusters that are typically normal and one cluster that is abnormal. We used optics and skmeans functions in R to implement OPTICS and CLUTO, respectively.

To investigate the clusters generated by CLUTO algorithm objectively, we calculated the specificity and sensitivity of CLUTO applied to the original data with 420 parameters. The specificity of identifying healthy eyes from eyes with keratoconus was 97.4% and the sensitivity of identifying eyes with keratoconus from healthy eyes was 96.3%. However, we selected DBSCAN applied on tSNE since this combination provided an acceptable accuracy and well-separated clusters matched with different stages of keratoconus.

The major finding of our study is that automated, unsupervised clustering algorithms using topographic, tomographic, and thickness profiles of cornea provides a specific and sensitive means for determining keratoconus status and severity. The proposed unsupervised machine learning analysis for keratoconus diagnosis and staging provides a promising tool for improving the early detection of initial stages of keratoconus and for potential monitoring of treatment for the disease.

Marc Amsler first described how keratoconus manifests in altered corneal topography in 1938; however, the introduction of computer-aided videokeratoscopy in the early 1980's revolutionized the diagnosis of keratoconus. Most of the early methods and severity indexes for identifying keratoconus have subsequently been based on corneal topography (see Non-Patent Documents 2, 4, 9, and 22-25). More recently it was determined that pachymetric indices were better able to differentiate healthy eyes from eyes with keratoconus, based on a cohort of 44 eyes with keratoconus and 113 healthy eyes (Non-Patent Document 26). However, in the current study we used topography, elevation, and thickness profiles of corneal extracted from optical coherence tomography (OCT) images from subjects using the SS-1000 Casia to identify and stage keratoconus.

Historically, classification of the stages of keratoconus has been based on qualitative analysis of overall corneal morphology. However, we used machine learning because it addresses limitations of currently used diagnosis methods, including qualitative rather than quantitative parameter assessments and observer bias. While machine learning algorithms for keratoconus have been previously proposed, most are based on either a single type of corneal parameter (e.g., topography alone) (Non-Patent Documents 23-25) or require pre-labeled data (Non-Patent Documents 4, 7 and 27). For instance, some researchers have used supervised neural network or tree-based classification to discriminate between normal eyes and eyes with keratoconus (Non-Patent Documents 4 and 27-29). However, pre-labeling an eye as keratoconus or forme fruste keratoconus subjectively itself is prone to subjective evaluation and bias.

We used approximately 420 corneal parameters generated by Casia instrument through swept source OCT images of the cornea. All these corneal parameters were transformed to a 2-D space using linear PCA and non-linear tSNE followed by an unsupervised machine learning algorithm. Therefore, we first extract the information that is highly predictable of the corneal status instead of feeding all parameters to the machine learning and confuse its prediction. However, most of the machine learning algorithms in the literature simply input different corneal parameters to a machine learning algorithm to identify keratoconus without leveraging the power of data transformation and extracting most informative knowledge for identifying disease.

To investigate whether PCA alone is able to generate well-separated clusters comparable to those identified by the combination of the PCA and tSNE, we applied PCA alone and performed clustering. We found that PCA alone generated clusters with significant overlap. We also applied CLUTO on the selected principal component to compare the outcome with tSNE and observed similar overlapping clusters (FIG. 5, top right).

Subjective assessment of the quality of learning using visualization of the clusters and overlaying the ESI keratoconus index of the Casia (as shown in FIG. 4) revealed that the ESI index of anterior corneal surface is highly correlated to the keratoconus severity of the eyes we identified in clusters. Specifically, the eyes in the Cluster IV (color coded white-triangular black) and classified as having advanced keratoconus by machine learning, have high agreement with anterior, posterior, and overall ESI indices since almost all eyes in this cluster have black.

The same analogy holds for eyes in Cluster I (color coded black) classified as normal, based on machine learning. However, for Cluster III (small cluster, color coded light gray), which represents mild keratoconus based on machine learning, eyes generally have a worse posterior ESI index compared to their anterior ESI index (FIG. 4, left and middle panels). This finding may suggest that posterior corneal parameters better identify keratoconus; however, this finding needs further investigation. We also hypothesize that eyes, labeled as normal by Casia ESI labeling system, falling in this cluster are likely "forme fruste" keratoconus candidates which need more attention from clinicians. Finally, Cluster II (color coded dark gray) that represents healthy eyes and eyes suspect of keratoconus based on machine learning, is in strong agreement with all ESI indices except at the far right tail. The eyes in this region are not in a good agreement with anterior and overall ESI indices. We hypothesize that this region could be a either a separate cluster or part of cluster III that we were unable to identify based on current data and algorithms used. It is also possible that the eyes in this small region have other eye conditions along with mild keratoconus for which we did not have enough information to characterize. However, FIG. 4 (middle panel) indicates that the posterior ESI index was more effective than anterior ESI index (FIG. 4, left panel). In fact, a study conducted by the Ambrosio group shows that posterior features are superior to anterior features in identifying keratoconus (Non-Patent Document 30).

To objectively assess the clinical labels we assigned to clusters with the severity of eyes in those clusters, we assessed the number of eyes with either large or small ESI. All eyes in Cluster IV (advanced keratoconus by machine learning) had ESI index greater than 38. In this group 71 (out of 81) eyes had ESI greater than 60, which indicates advanced stages of keratoconus. For Cluster I (normal by machine learning), only seven eyes (out of 256) had an ESI index greater than 30, indicating that the overwhelming majority of eyes in this cluster were normal. Therefore, our clustering is in good agreement with ESI at the two sides of spectrum. Based on Casia ESI diagnosis labels, the specificity of our machine learning method in identifying normal from keratoconus eyes was 94.1% and the sensitivity of identifying keratoconus from normal eyes was 97.7%, considering only normal and advanced keratoconus clusters.

There are a number of limitations to our study which could be addressed in follow-up studies. We compared the clustering outcome with Casia ESI index and showed that there is a good agreement between our finding and ESI index spectrum (FIGS. 3 and 4). However, to assess the generalizability of this unsupervised clustering approach method, it needs to be validated by other keratoconus indices such as Bellin-Ambrosio (BA) index. Therefore, it is required to conduct another study to confirm how this approach is generalizable to corneal parameters generated by Pentacam instrument by accessing such datasets. Also, the accuracy of this approach can be validated if the clinical diagnosis labels of all eyes were available. However, accessing clinical diagnosis labels for all eyes in such big datasets is a challenging and tedious task. Nevertheless, it is beneficial to assess the proposed approach in a follow-up study with a dataset that includes clinical diagnosis labels.

We performed a qualitative and quantitate assessment to determine whether PCA alone or other clustering approaches generate well-separated clusters. We found that the OPTICS density-based clustering approach was able to segregate eyes at different stages of keratoconus while the CLUTO unsupervised clustering approach generated overlapping clusters. However, the most important aspect of our proposed approach lies in the visualization property and the tSNE 2-D map. This is critical in practical clinical settings in which it is more appropriate to monitor the progression of the diseases on a 2-D map rather than proposing a black-box without 2-D visualization.

In summary, we proposed a possible solution to address shortcomings of current approaches in keratoconus diagnosis and monitoring, including observer bias in pre-defining diagnosis and limitations in the providing only a binary outcome that the eye belongs to either normal or disease group. The introduced unsupervised machine learning algorithm requires no pre-labeled data for training and can automatically identify the keratoconus status of a given eye based on comprehensive corneal parameters, including topography, elevation, and thickness profiles. More importantly, it provides visualization of the status of the eye compared to other eyes at different stages of keratoconus which was lack in supervised machine learning methods. To the best of our knowledge, this is the first attempt to develop a fully unsupervised algorithm for keratoconus identification and monitoring.

Keratoconus status and severity can now be well identified using automated unsupervised clustering algorithms using topographic, tomographic, and thickness profiles of cornea. This approach can be used in corneal clinics and research settings to better diagnose, monitor changes and progression and improve our understanding of corneal changes in keratoconus.

It should be understood that the present invention can be used in many different ways and for many different applications to dramatically improve the corneal severity identification.

The invention claimed is:

1. A method for assisting corneal severity identification, the method comprising:
    obtaining a corneal configuration data set of a cornea to be examined by a tomography;
    visualizing the corneal configuration data set of the cornea to be examined along with a number of pre-existing corneal configuration data sets of disorder corneas, disorder-suspect corneas and normal corneas obtained by the tomography using t-distributed Stochastic Neighbor Embedding in a two or three dimensional map, and
    locating a visualized part of the corneal configuration data set of the cornea to be examined on the map to judge corneal severity from a cluster which the located visualized part belongs to, wherein the cluster comprises visualized parts of the pre-existing corneal configuration data sets of disorder corneas, disorder-suspect corneas or normal corneas.

2. The method according to claim 1, wherein the tomography is an optical coherence tomography.

3. A method for assisting corneal severity identification, the method comprising:
    obtaining a corneal configuration data set of a cornea to be examined by a tomography;
    visualizing the corneal configuration data set of the cornea to be examined along with a number of pre-existing corneal configuration data sets of disorder corneas, disorder-suspect corneas and normal corneas obtained by the tomography using t-distributed Stochastic Neighbor Embedding in a two or three dimensional map, and
    judging corneal severity from the map;
    wherein the corneal severity is at least one selected from the group consisting of keratoconus severity, bullous keratopathy severity, walleye severity, keratoleukoma severity, keratohelcosis severity, herpes corneae severity, corneal chemical burn severity, corneal thermal burn severity, and degeneratio corneae severity.

4. A method for assisting corneal severity identification, the method comprising:
    obtaining a corneal configuration data set of a cornea to be examined by a tomography;
    visualizing the corneal configuration data set of the cornea to be examined along with a number of pre-existing corneal configuration data sets of disorder corneas, disorder-suspect corneas and normal corneas obtained by the tomography using t-distributed Stochastic Neighbor Embedding in a two or three dimensional map, and
    judging corneal severity from the map;
    wherein the corneal configuration data set comprises at least one of a 2D analysis of ACA viewing surface, a 2D analysis of CCT/ACD viewing surface, STAR360°, analysis of lens morphology on 2D Result, analysis of lens morphology on 3D Result, analysis of corneal morphology and reference point.

5. The method according to claim 4, wherein the 2D analysis of ACA viewing surface comprises at least one of AOD500, A0D750, ARA500, ARA750, TISA500, TISA750, TIA500, and TIA750.

6. The method according to claim 4, wherein the 2D analysis of CCT/ACD viewing surface comprises at least one of CCT, ACD Endo., LV, ACW, CCT, ACD[Epi.], ACD[Endo.], Vault, CLR and ATA.

7. The method according to claim 4, wherein the STAR360° comprises at least one of AOD250, AOD500, AOD750, ARA250, ARA500, ARA750, TISA250, TIA500, TIA750, CCT, ACD Endo., LV, ACW, AC.Area, IT750, IT2000, I-Curv. and ITC.

8. The method according to claim 4, wherein the analysis of lens morphology on 2D Result comprises at least one of Front R, Thickness, Diameter, Decentration and Tilt.

9. The method according to claim 4, wherein the analysis of lens morphology on 3D Result comprises at least one of Front R, Front Rs, Front Rf, Back R, Back Rs, Back Rf, Thickness, Diameter, Decentration, and Tilt.

10. The method according to claim 4, wherein the analysis of corneal morphology comprises at least one of Ks, Kf, CYL, ACCP, ECC, AA, Apex, Thinnest, and ESI.

11. The method according to claim 4, wherein the reference point comprises at least one of SS, AR, IR, IRT, and EP.

12. A method for assisting corneal severity identification, the method comprising:
    obtaining a corneal configuration data set of a cornea to be examined by a tomography;
    visualizing the corneal configuration data set of the cornea to be examined along with a number of pre-existing corneal configuration data sets of disorder corneas, disorder-suspect corneas and normal corneas obtained by the tomography using t-distributed Stochastic Neighbor Embedding in a two or three dimensional map, and
    judging corneal severity from the map;
    wherein the corneal configuration data set comprises at least one of DSI, OSI, CSI, SD_P(4 mm), CV_P(4 mm), ACP(3 mm), RMS_E(4 mm), SR_E(4 mm), SR_H(4 mm), CSI_T, SD_T(4 mm), and CV_T(4 mm).

13. A method for assisting corneal severity identification, the method comprising:
    obtaining a corneal configuration data set of a cornea to be examined by a tomography;
    visualizing the corneal configuration data set of the cornea to be examined along with a number of pre-existing corneal configuration data sets of disorder corneas, disorder-suspect corneas and normal corneas obtained by the tomography using t-distributed Stochastic Neighbor Embedding in a two or three dimensional map, and
    judging corneal severity from the map;
    wherein the tomography is an anterior eye part optical coherence tomography.

14. A method for assisting corneal severity identification, the method comprising:

obtaining a corneal configuration data set of a cornea to be examined by a tomography;

visualizing the corneal configuration data set of the cornea to be examined along with a number of pre-existing corneal configuration data sets of disorder corneas, disorder-suspect corneas and normal corneas obtained by the tomography using t-distributed Stochastic Neighbor Embedding in a two or three dimensional map, and judging corneal severity from the map;

wherein the tomography is a swept-source optical coherence tomography.

* * * * *